United States Patent [19]

Huebner

[11] Patent Number: 4,600,718
[45] Date of Patent: * Jul. 15, 1986

[54] METHOD OF TREATING WEIGHT LOSS DISORDERS

[76] Inventor: Hans F. Huebner, 106 Beach Ave., Larchmont, N.Y. 10538

[*] Notice: The portion of the term of this patent subsequent to Oct. 8, 2002 has been disclaimed.

[21] Appl. No.: 742,223

[22] Filed: Jun. 6, 1985

Related U.S. Application Data

[63] Continuation of Ser. No. 651,594, Sep. 18, 1984, Pat. No. 4,546,103.

[51] Int. Cl.$^4$ ............................................. A61K 31/44
[52] U.S. Cl. .................................................... 514/282
[58] Field of Search ......................................... 514/282

[56] References Cited

U.S. PATENT DOCUMENTS 4,217,353 8/1980 Smith, Jr. ............................. 514/282

Primary Examiner—Stanley J. Friedman
Attorney, Agent, or Firm—Hopgood, Calimafde, Kalil, Blaustein & Judlowe

[57] ABSTRACT

There is disclosed a method of treating weight loss disorders. This method consists essentially of administering to a mammal, such as a human, a daily dosage of at least about 10 milligrams per 37 kilogram body weight of at least one opiate antagonist. These opiate antagonists include naloxone, naltrexone, nalorphine, diprenorphine, levallorphan, pentazocine, metazocine, cyclozocine, etazocine, and pharmacologically acceptable salts thereof. The use of naloxone hydrochloride as the opiate antagonist is preferred.

2 Claims, No Drawings

METHOD OF TREATING WEIGHT LOSS DISORDERS

CROSS REFERENCE TO RELATED APPLICATION

This application is a continuation of my copending application Ser. No. 651,594, filed Sept. 18, 1984, now U.S. Pat. No. 4,546,103, and entitled METHOD OF TREATING WEIGHT LOSS DISORDERS.

BACKGROUND OF THE INVENTION

This invention relates generally to the use of narcotic antagonists, including naloxone and naltrexone, to counteract the physiological and/or psychological effects of starvation by food and fluid deprivation in animals, including humans. In particular, this invention relates to a method for treating mammals, including humans, with opiate antagonists in order to alleviate weight loss disorders, including anorexia nervosa and bulimia.

Deprivation of food and fluids leading to starvation with accompanying weight loss may be imposed by "circumstances", as, for example, famine, or by others, as, for example, a prisoner of war situation. It may also be self imposed, as in the case of anorexia nervosa and bulimia.

The term "anorexia" refers to a medical symptom indicating a lack or loss of appetite for food (see Dorland's Medical Dictionary, 25th Ed.) which may occur in a variety of medical conditions and diseases. In contrast, the term "anorexia nervosa" denotes a diagnosis of a severe nervous condition characterized by a relentless addiction-like pursuit of thinness to the point of cachexia by voluntarily withholding foods and fluids, and, at times, by excessive exercising, that results from dieting to achieve a socially pleasing slim appearance.

Anorexia nervosa is also associated with physiological changes that include abnormal endocrine and metabolic functions, variations from normal urine concentrations, and a lowering of body temperature, respiratory, and cardiovascular functions. These changes appear to be part of a universal adaptive mechanism of starvation since they are reversible with weight gain and do not differ substantially from those found in other forms of starvation, such as famine or prisoner of war situations.

Bulimia is characterized by excessive intake of food and fluids followed by, or associated with, purgatory maneuvers designed to rid oneself of the ingested food and fluids. Such purgatory self-manipulations include, but may not be restricted to vomiting, use of laxatives and rectal enemas, and depletion of body fluids by diuretic agents. Each of these methods leads to body fluid loss and disturbance of the body's electrolyte balance. Excessive food intake and purging behavior usually results from excessive dieting and can become an addictive compulsive habit, especially in distressed and depressed individuals.

Opiate antagonists are synthetic compounds which may be given to opiate addicts to block the physical and/or psychological effects of opiates. These opiate antagonists include naltrexone and naloxone.

Naloxone is a powerful antagonist of exogenous opiates and naturally occurring opioid peptide hormones which have opiate like effects on the organism. It is a relatively pure opiate antagonist and is administered intravenously. Naltrexone is known to be a powerful antagonist of exogenous opiates and naturally occurring opioid peptide hormones which have opiate like effects on the organism. It may be prepared in accordance with the teachings of U.S. Pat. No. 3,322,950 and Canadian Pat. No. 913,077. Naltrexone is a relatively pure opiate antagonist and is effective when given orally.

Naltrexone has been used in the past to induce anorexia as discussed in U.S. Pat. No. 4,217,353. In that patent, there is discussed certain studies directed principally to the safety and efficacy of naltrexone as an oral narcotic antagonist. In these studies, the patentee notes that there are some isolated and contradictory statements concerning the effect of naltrexone on appetite in man.

One study has suggested the use of naloxone in treating anorexia nervosa. See Moore et al "Naloxone in the Treatment of Anorexia Nervosa: Effect on Weight Gain and Lipolysis", 74 J. Roy. Soc. Med. 129 (1981). This study of the effect of naloxone on anorexics is inconclusive, however, because the naloxone treatment was coupled with hypercaloric feeding (3000–4000 kcal dietary intake) as well as the administration of antidepressant medication (usually amitriptylene). A letter in that same publication suggests that the weight gain described in the Moore et al study might be related to interference with vomiting, both voluntary and involuntary. It also discusses a possible role of opiate antagonists in the therapy of anorexia nervosa. 74 J. Roy. Soc. Med. 631. The "vomiting" explanation was subsequently discussed and dismissed by a co-author of the Moore et al article. 74 J. Roy. Soc. Med. 945.

The search has continued for improved methods of treating weight loss disorders such as anorexia nervosa and bulimia. This invention was made as a result of that search.

OBJECTS AND SUMMARY OF THE INVENTION

Accordingly, it is a general object of the present invention to avoid or substantially alleviate the above-discussed problems of the prior art.

A more specific object of the present invention is to provide a method for treating weight loss disorders wherein the physiological and/or behavioral changes which result from these disorders are reversed and the patient is not subjected to harmful side effects.

A further object of the present invention is to provide for weight gain in a patient afflicted with anorexia nervosa.

Another object of the present invention is to eliminate the self-destructive excessive food intake and purging behavior in patients afflicted with bulimia, which leads to loss of body fluids and electrolyte imbalance.

Still other objects and advantages of the present invention will become apparent from the following summary of the invention and description of its preferred embodiments.

The present invention provides a method of treating weight loss disorders. This method comprises administering to a mammal, such as a human, a daily dosage of at least about ten milligrams per 37 kilogram body weight of an opiate antagonist. The opiate antagonist may be naloxone, naltrexone, nalorphine, diprenorphine, levallorphan, pentazocine, metazocine, cyclozocine, etazocine, or pharmacologically acceptable salts thereof. Mixtures of two or more opiate antagonists may also be used.

The present invention is based, in part, on the discovery that prolonged starvation triggers a physical and mental adaptive mechanism that is mediated by endogenous opioid peptides or endorphins. Increased preoccupation with food as well as a reduction of the body metabolism and a numbing of the psychological effects of starvation appear to be the essential features of this mechanism. Consistent with these features, anorexia nervosa is not associated with a loss of appetite, as earlier thought, but is characterized by an increasing preoccupation with food and intensified food related activities including a powerful urge to eat as dieting progresses. This urge is resisted by anorexics for the sake of benefitting from the sense of well-being mediated by elevated levels of endorphins.

Endorphins are powerful enforcers which produce tolerance and dependence by mediating cellular mechanisms of addiction. In sufficient concentration, they provide a sense of well-being. Most anorexics initiate a starvation diet to counteract a sense of distress and/or depression. This sense of well-being provided by the endorphins makes anorexics susceptible to the addictive effects of the endorphins. Once the addictive mechanism is initiated, the need to overcome tolerance to the reinforcing effects of the endorphins causes the anorexic to seek progressively lower weight which, absent intervention such as by the method of the present invention, can ultimately lead to death.

The present invention is also based, in part, on the discovery that endogenous opioid peptides are triggered by the purgatory acts performed by bulimics. These peptides are the reinforcing substrate which motivates and perpetuates bulimic behavior consistent with the pattern of addiction.

Opiate antagonists, such as naloxone and naltrexone, act as powerful antagonists of endogenous opiates and naturally occurring opioid peptide hormones by blocking the receptor sites, and thus the euphoria-producing effects, of opiates. Once self-starvation no longer "feels good", as a result of this blockage, the patient may be induced to follow a prescribed diet which, in combination with appropriate psychotherapy, will enable weight gain and the correction of physiological and/or behavioral problems associated with the weight loss disorder.

The use of minor amounts of opiate antagonists will not effectively counteract the effects, including the addictive effects, of the endorphins. While the use of minor amounts of opiate antagonists, such as the amounts disclosed in the above-discussed Moore et al article, may have an effect vis-a-vis lipolysis, such amounts are substantially ineffective to counteract the addictive and other effects of the endorphins.

DESCRIPTION OF THE PREFERRED EMBODIMENTS

As noted above, the present invention is directed to a method of treating weight loss disorders such as anorexia nervosa and bulimia. The method consists essentially of administering to a mammal, such as a human, a daily dosage of generally at least about 10, typically from about 30 to about 200, and preferably from about 50 to about 150 milligrams of an opiate antagonist based upon a 37 kilogram body weight.

These opiate antagonists include naloxone, naltrexone, nalorphine, diprenorphine, levallorphan, pentazocine, metazocine, cyclozocine, etazocine, and pharmacologically acceptable salts thereof. Mixtures of two or more opiate antagonists may also be used.

These opiate antagonists are described above in terms of their common names. They may also be described in terms of their chemical names. Naloxone, for example, is also known as N-allylnoroxymorphone; naltrexone is (−)-17-(cyclopropylmethyl)-4,5,-alpha-epoxy-3,14-dihydroxymorphinan-6-one; nalorphine is the alkyl derivative of morphine, i.e., N-allynormorphine; levallorphan is 1-N-allyl-3-hydroxynorphinan; and pentazocine is 2-dimethylallyl-5,9-dimethyl-2′-hydroxy-benzomorphan.

Naloxone, naltrexone and/or their pharmacologically acceptable salts are preferred for use in the present invention. Naloxone and its pharmacologically acceptable salts are administered intravenously whereas naltrexone and its pharmacologically acceptable salts are administered orally. Naloxone hydrochloride is particularly preferred.

The opiate antagonist is administered either orally or intravenously for a time sufficient to allow the patient's weight to increase and to break the addictive effect of the opiates. This time period may vary widely and is dependent upon the circumstances in a particular case.

This invention is further illustrated by the following Examples.

EXAMPLES

Nine female hospitalized adolescents, who fulfill the Research Diagnostic Criteria for anorexia nervosa, as described in Feighner et al in "Diagnostic Criteria For Use In Psychiatric Research", 26 Arch. Gen. Psychiatry 57 (1972), and who have a body weight of approximately 37 kilograms, are treated with naloxone, naltrexone, and placebo drugs commercially available from DuPont Pharmaceuticals, Inc. Naloxone hydrochloride is dissolved in sufficient normal saline solution to be infused over a four hour period. Four different dosages (0.2; 0.4; 0.8; and 1.2 milligrams per kilogram of body weight) are administered over a four hour period to each patient in the study. One four hour administration is provided on every other day. Each day of naloxone treatment is followed by a day of placebo treatment in a double blind arrangement comprising a four hour intravenous infusion of a placebo consisting of the inert ingredients of naloxone hydrochloride dissolved in normal saline solution.

Naltrexone is orally administered to one patient having a body weight of approximately 32 kilograms in four increasing daily dosages of 25, 50, 75, and 100 milligrams with each of the dosages matched by a placebo on alternate days in double blind fashion.

The endorphin dependent hormone levels measured in these subjects show less response to endorphin receptor blockade by naloxone than the response of the same hormones to naloxone administration in normal healthy volunteers. Furthermore, several behavioral observations made on days of opiate antagonist administration suggest a powerful effect of endorphins on the regulation of coping, mood, and eating behavior. Only for the duration of the pharmacological action of naloxone these subjects displayed a marked change. The well-known hypervigilant, manipulative irritable, restless, reticent and angry behavior changed for about 12-24 hours into a state of quiet, tearful weeping for no apparent reason, of wishing someone close for comfort and sharing of worried thoughts, and of apparent defenselessness. Furthermore, the usual avoidance of food and anxiety related to a fear of obesity gave way to one of quietly accepting the prescribed diet and enlisting encouragement from staff. These changes occur under opiate antagonist, but not placebo, administration. Also, these changes are more apparent with increasing opiate antagonist dosage.

The principles, preferred embodiments, and modes of operation of the invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

I claim:

1. A method of treating weight loss disorders consisting essentially of administering to a mammal having a weight loss disorder a daily dosage of an effective amount which consists essentially of at least about 10 milligrams per 37 kilogram body weight of at least one opiate antagonist.

2. The method of claim 1 wherein said mammal is a human.

* * * * *